US008252326B2

(12) United States Patent
Lin

(10) Patent No.: US 8,252,326 B2
(45) Date of Patent: Aug. 28, 2012

(54) SELF-MICROEMULSIFYING DOSAGE FORMS OF LOW SOLUBILITY ACTIVE INGREDIENTS SUCH AS CO-ENZYME Q10

(75) Inventor: Jing Lin, Mulgrave (AU)

(73) Assignee: Catalent Australia Pty Ltd., Braeside, Victoria (AU)

( * ) Notice: Subject to any disclaimer, the term of this patent is extended or adjusted under 35 U.S.C. 154(b) by 264 days.

(21) Appl. No.: 11/141,774

(22) Filed: Jun. 1, 2005

(65) Prior Publication Data

US 2006/0275358 A1    Dec. 7, 2006

(51) Int. Cl.
*A61K 9/48* (2006.01)
(52) U.S. Cl. ........................ 424/451; 424/94.1; 424/455
(58) Field of Classification Search .................. None
See application file for complete search history.

(56) References Cited

U.S. PATENT DOCUMENTS

| | | | |
|---|---|---|---|
| 4,869,900 A | 9/1989 | Pozzi et al. | 524/94.1 |
| 5,179,122 A | 1/1993 | Greene et al. | 514/458 |
| 5,364,632 A | 11/1994 | Benita et al. | 424/450 |
| 5,443,842 A | 8/1995 | Seghizzi et al. | 424/456 |
| 5,480,865 A | 1/1996 | Kingham | 514/2 |
| 5,536,729 A | 7/1996 | Waranis et al. | 514/291 |
| 5,889,062 A | 3/1999 | Hoppe et al. | 514/690 |
| 5,912,272 A | 6/1999 | Hoppe et al. | 514/678 |
| 5,989,583 A | 11/1999 | Amselem | 424/439 |
| 5,993,858 A * | 11/1999 | Crison et al. | 424/490 |
| 6,007,826 A | 12/1999 | Benita et al. | 424/401 |
| 6,054,136 A * | 4/2000 | Farah et al. | 424/400 |
| 6,056,971 A | 5/2000 | Goldman | 424/439 |
| 6,191,172 B1 | 2/2001 | Borowy-Borowski et al. | 514/772.4 |
| 6,261,575 B1 | 7/2001 | Hoppe et al. | 424/401 |
| 6,337,045 B1 | 1/2002 | Grosswald et al. | 264/402 |
| 6,403,116 B1 | 6/2002 | Anderson et al. | 424/439 |
| 6,428,779 B1 | 8/2002 | Sauermann et al. | 424/78.03 |
| 6,720,001 B2 | 4/2004 | Chen et al. | 424/456 |
| 6,740,338 B1 | 5/2004 | Chopra | 424/456 |
| 2004/0152612 A1 | 8/2004 | Supersaxo et al. | 510/407 |
| 2005/0069582 A1 | 3/2005 | Fantuzzi | 424/456 |
| 2005/0070611 A1 | 3/2005 | Fantuzzi | 514/690 |

FOREIGN PATENT DOCUMENTS

| | | |
|---|---|---|
| EP | 0751762 | 12/2000 |
| EP | 1249230 | 10/2002 |
| EP | 0859592 | 5/2003 |
| WO | WO 95/26180 | 10/1995 |
| WO | WO 95/26181 | 10/1995 |
| WO | WO 95/26182 | 10/1995 |
| WO | WO 97/12591 | 4/1997 |
| WO | WO 97/36577 | 10/1997 |
| WO | WO 99/39700 | 8/1999 |
| WO | WO 02/083098 | 10/2002 |
| WO | WO 2005/000258 | 1/2005 |

OTHER PUBLICATIONS

Palamakula et al., AAPS PharmSciTech, 2004, vol. 5, No. 4, Article 66, p. 1-8.*
Douwes & Hassan, Business Briefing: Pharamagenerics, 2003, p. 1-3.*
Kommuru et al., International Journal of Pharmaceutics, 2001, vol. 212, p. 233-246.*
Palamakula et al., AAPS PharmSciTech 2004, vol. 5, No. 4, Article 66, p. 1-8.*
Nandi et al., AAPS PharmSciTech 2003, vol. 4, No. 1, Article 10, p. 1-9.*
Pouton C.W., European Journal of Pharmaceutical Sciences, 2000, vol. 11, Suppl. 2, p. S93-S98.*
Kim et al., Drug Development and Industrial Pharmacy, vol. 26, No. 5, p. 523-529.*
Kommuru et al., International Journal of Pharmaceutics, 2001, vol. 212, p. 233-246.*
Palamakula et al., AAPS PharmSciTech 2004, vol. 5, No. 4, Article 66, p. 1-8.*
Nandi et al., AAPS PharmSciTech 2003, vol. 4, No. 1, Article 10, p. 1-9.*
Gursoy & Benita, Biomedicine & Pharmacotherapy, Apr. 2004, vol. 58, p. 173-182.*
Palamakula, A., Ph.D. Thesis, May 2004, Biopharmaceutical and development of limonene-based self-nano-emulsified capsule dosage form of coenzyme Q-10, 256 pages.*
Kahlweit et al., Langmuir, 1997, vol. 13, 5249-5251.*
"Title page", Texas Tech University, "Electronic Thesis and Dissertations" web page, Palamakula, A. title page thesis/dissertaion information, pp. 1-2.*
"Details", Palamakula, Anitha, Thesis, 1 page.*
Douwes & Hassan, Business Briefing: Pharamagenerics 2003, p. 1-3.*
Kim et al., Drug Development and Industrial Pharmacy, 2000, vol. 26, No. 5, p. 523-529.*
"Title page", Texas Tech University, "Electronic Thesis and Dissertations" web page, Palamakula, A. title page thesis/dissertaion information, pp. 1-2, downloaded on 2011.*
"Details", Palamakula, Anitha, Thesis, 1 page, downlaoded on 2011.*

* cited by examiner

*Primary Examiner* — Kade Ariani
(74) *Attorney, Agent, or Firm* — Fitzpatrick, Cella, Harper & Scinto

(57) ABSTRACT

The invention includes dosage formulations, dosage forms and related methods for providing oral dosage forms of low solubility active ingredients such as coenzyme Q10. The present invention includes a Self-Microemulsifying Drug Delivery System (SMEDDS) in the form of a self-microemulsifying mixture that comprises a combination of a hydrophilic surfactant and a lipophilic co-surfactant (forming a surfactant pair). The preferred surfactant pair comprises a hydrophilic surfactant and a lipophilic co-surfactant with respective HLB (Hydrophile-Lipophile Balance) values of more than 12 and less than 8 respectively. The systems also contain at least one lipophilic solvent. The formulations exhibited excellent dissolution properties and storage stability.

10 Claims, No Drawings

SELF-MICROEMULSIFYING DOSAGE FORMS OF LOW SOLUBILITY ACTIVE INGREDIENTS SUCH AS CO-ENZYME Q10

CROSS-REFERENCE TO RELATED APPLICATIONS

None.

FIELD OF THE INVENTION

The present invention regards methods and formulations related to dosage forms of coenzyme Q10 and similar low solubility active ingredients.

BACKGROUND OF THE INVENTION

Coenzyme Q10 is a lipophilic (i.e. hydrophobic) pharmaceutical or nutrient substance with very low solubility in water (practically insoluble in water). Formulations of coenzyme Q10, e.g. for oral administration, are therefore mainly based on the use of oils or similar excipients as the carrier media. The products for oral administration formulated in this way and currently available commercially, such as, for example, Super Bio-Quinone (Pharma Nord, a Danish pharmaceutical company) and GNC preventive nutrition CoQ-10 (General Nutritional Corp.) have a very low bioavailability.

Common soft capsule formulations are solutions in oils or suspensions in lipophilic systems. Bioavailability studies from various publications have shown low bioavailability of Q10 in those conventional formulations. It is also known that conventional soft capsule products of Q10 have zero or very low dissolution.

In the case of Q10, in the past it has been dissolved in oils and emulsified by surfactants. However, conventional emulsions resulted from self-emulsifying systems often gave coarse droplets that are at micron ($\mu$) scale. The droplet size distributions are often broad, ranging from about 1 to 100 micron.

The coarse droplet size and broad distribution are believed to be the main contributors to inconsistent dissolution behavior of coenzyme Q10 in soft capsule formulations. This behavior is believed to be dependent on density of the droplets which in turn are dependent on the ratio of oil to surfactants. Furthermore, the formation of conventional emulsions requires strong agitation. This is difficult to attain by the rotational speed of dissolution paddles (commonly less than 100 rpm).

In contrast to conventional emulsions, microemulsions are isotropic and produce droplet sizes in the nanometer range, typically less than 100 nm. The polydispersity is often narrow. The formation of microemulsions is typically fast, thermodynamically stable and thus, does not require vigorous stirring. It is a common procedure in dissolution testing that samples withdrawn are filtered through a 0.45 micron (or 450 nm) membrane filter. A microemulsion would have no problem in passing through the filter, while a conventional emulsion would risk broken droplets and active ingredients retained on the filter due to its hydrophobicity.

It is well known that soft capsules are limited by the amount of water that is in fill formulations, such that microemulsions cannot be encapsulated in the typical shell formulation. Accordingly, it is only practical to encapsulate the precursors of microemulsions that do not contain water, and that are capable of forming microemulsions upon contact with water. Such precursors are referred to as Self-Microemulsifying Drug Delivery Systems or SMEDDS.

Prior fill formulations in the form of oil-based soft capsules continue to have difficulty providing optimum bioavailability owing to the low solubility of CoQ10, and the tendency of the product to crystallize over time.

The problems to be solved by the present invention include increasing bioavailability while preventing crystallization of the CoQ10 active ingredient upon release. The present invention is further directed to providing dosage forms providing enhanced dissolution of Q10 for improved bioavailability. In addition, the present invention provides fill formulations that may be used effectively in soft capsule dosage forms.

SUMMARY OF THE INVENTION

The problem addressed by the present invention is the dispersion of Coenzyme Q10 (ubiquinone) ("CoQ10") for the purposes of preparing dosage forms, especially soft capsule dosage forms.

In general terms, the invention includes fill formulations, dosage forms, and related methods for providing low solubility active ingredients such as coenzyme Q10. These include fill formulations for soft capsules comprised of: (1) a hydrophobic therapeutic agent which has a water solubility less than 2% by weight; (2) a solubilizing system which is capable of self-microemulsifying upon contact with water, comprising (a) at least one hydrophobic solvent; (b) at least one hydrophobic/lipophilic surfactant (co-surfactant); (c) at least one hydrophilic surfactant (surfactant); and optionally a hydrophilic solvent.

The present invention includes a Self-Microemulsifying Drug Delivery Systems (SMEDDS) in the form of a self-emulsifying mixture that comprises a combination of a hydrophilic surfactant and a lipophilic co-surfactant (forming a surfactant pair). The preferred surfactant pair comprises a hydrophilic surfactant and a lipophilic co-surfactant with respective HLB (Hydrophile-Lipophile Balance) values of more than 12 and less than 8 respectively. It is also preferred that the ratio of the hydrophilic surfactant to the lipophilic co-surfactant is in the range of from about 30:1, to about 3:1, the ratio of the surfactant to the co-surfactant depending on the HLB values of the individual surfactants and the polarity of the hydrophobic solvents used. The amount of hydrophobic solvents in the total of the excipients can range from 10-60% by weight, preferably 20-50% by weight, to maximize the loading of active ingredients.

Examples of hydrophilic surfactants that may be used in the present invention include polyethylene-glycol (PEG) fatty acid esters, PEG esters, PEG ethers, and PEG glycerides, such as PEG 35 Castor oil (Etocas 35, Croda), Polysorbate® 85 (or Crillet 45, Croda), Polysorbate® 80 (or Crillet 4, Croda), PEG 40, hydrogenated castor oil (e.g., Cremophor RH40, BASF), and saturated polyglycolysed glycerides (Labrafac Hydro WL1219, Gattefosse, France).

Examples of lipophilic co-surfactants that may be used in the present invention include non-ionic surfactants with HLB values less than 8, such as macrogolglycerides, sorbitan esters and mono- and diglycerides, glycol mono and diesters, glyceryl esters, PEG esters, such as linoleoyl macrogolglycerides (e.g., Labrafil M 2125 from Gattefosse, France), oleoyl macrogolglycerides (e.g., Labrafil M 1944 from Gattefosse, France), propylene glycol laurate (e.g., Lauroglycol FCC from Gattefosse, France), glyceryl mono-oleate (Croda), Span 80 (Croda), and medium chain mono- and di-glycerides (e.g., Capmul MCM C8 from Abitec Corporation, Columbus, Ohio).

It is preferred that the concentration of the hydrophilic surfactant in the self-emulsifying fill formulation is in the range of from about 20-70% by weight, and that the concentration of the lipophilic co-surfactant in the self-emulsifying mixture is in the range of from about 1.5-50% by weight.

The preferred embodiment of the self-emulsifying mixture also includes at least one hydrophobic solvent. It is also preferred that the concentration of the hydrophobic solvent(s) in the self-emulsifying fill formulation be in the range of from about 2-50%, preferably 10-40% by weight. Examples include one or more of the following or mixtures thereof: fatty acids, essential oils, aliphatic esters, triglycerides, such as oleic acid, isopropyl myristate, acetylated monoglycerides, medium chain triglycerides, peppermint oil, orange oil, and Lemon oil. It is preferred that the hydrophobic solvent comprises a combination of isopropyl myristate and Lemon oil.

The self-emulsifying mixtures of the present invention also preferably include at least one optional hydrophilic solvent or solubilizer, such as glycol ethers including diethylene glycol monoethyl ether (e.g. Transcutol® P, from Gattefosse, France), to facilitate reduction of droplet size. It is preferred that the ratio of the oil-surfactant-cosurfactant mixture to the solubilizer is about 10:0.2, preferably 10:1.

To prepare a soft capsule fill formulation, the self-emulsifying mixture of the present invention is combined with an active ingredient such as coenzyme Q10. This formulation in turn may be placed into soft capsules to prepare a dosage form. The inventive formulations can be prepared using conventional techniques known to those of skill in the art. The self-emulsifying mixtures of the present invention may also be advantageously applied to other low aqueous solubility active ingredients, such as those having water solubility less than about 2% by weight. Such low aqueous solubility active ingredients may include poorly water soluble therapeutic agents, pharmaceuticals, and health and nutritional ingredients. Examples include Loratadine, Vitamins A, D and E.

The present invention overcomes the principal problems associated with the poor solubility of CoQ10 in water and its tendency to crystallize over time. Also, as soft capsules cannot tolerate much water, the present invention provides a soft capsule with self-emulsifying properties leading to high bioavailability of water insoluble active ingredients such as CoQ10.

The formulations of the present invention result in translucent to clear liquids in water with no visible droplet formation, and give both release percentages and release rates that are superior to conventional formulations.

Thus, there is disclosed a composition comprising a self-emulsifying mixture comprising: (1) at least one hydrophilic surfactant; (2) at least one lipophilic co-surfactant, wherein the hydrophile-lipophile balance of said at least one hydrophilic surfactant is greater than 12 and the hydrophile-lipophile balance of said at least one lipophilic co-surfactant is less than 8; and (3) at least one hydrophobic solvent.

There is further disclosed a dosage form of a low solubility active ingredient, comprising: at least one low solubility active ingredient contained in a self-emulsifying mixture, said self-emulsifying mixture comprising: (1) at least one hydrophilic surfactant; (2) at least one lipophilic co-surfactant, wherein the hydrophile-lipophile balance of said at least one hydrophilic surfactant is greater than 12 and the hydrophile-lipophile balance of said at least one lipophilic co-surfactant is less than 8; and (3) at least one hydrophobic solvent.

There is also disclosed a dosage form of coenzyme Q10, comprising: coenzyme Q10 contained in a self-emulsifying mixture, said self-emulsifying mixture: (1) at least one hydrophilic surfactant; (2) at least one lipophilic co-surfactant, wherein the hydrophile-lipophile balance of said at least one hydrophilic surfactant is greater than 12 and the hydrophile-lipophile balance of said at least one lipophilic co-surfactant is less than 8; and (3) at least one hydrophobic solvent.

DETAILED DESCRIPTION OF THE PREFERRED EMBODIMENTS

In view of the foregoing Summary, the following describes the preferred embodiments of the present invention, which are presently considered to be the best mode thereof.

Solubility Studies

To determine suitable excipient systems for actives, solubility studies were carried out on a variety of constituents of the inventive SMEDDS formulations. The solubility of Q10 in various oils, surfactants and co-surfactants were determined by placing an excess of the Q10 (approximately 2.5 g) in 22.5 g of the vehicle in screw capped glass bottles and heating the mixture to 55° C. in a water bath to facilitate the solubilization. Mixtures were equilibrated at room temperature for 24 hours and then filtered through 0.45 µm membrane filter to separate the undissolved drug. One gram of the filtered liquid mixtures were then weighed and diluted with cyclohexane and quantified by UV/Visible Spectrometry. The results are shown in Table 1. Lemon oil and isopropyl myristate provided higher solubility than other oils. Although not limited to a theory of operation, it is believed that the oils form a distinct core in the interior of the surfactant aggregate when being dispersed in water, resulting in enhanced solubilizing capacity of the oils with improved drug loading capabilities of the emulsion.

Preparation of Vehicle Compositions

Lipophilic surfactants with hydrophilic-lipophilic balance (HLB) of less than 10 were found to promote some emulsification of the oil, but as a consequence, the emulsion droplets were found to be too coarse to be acceptable. Hydrophilic surfactants with hydrophilic-lipophilic balance (HLB) values of greater than 10 were found to be efficient in producing fine, uniform emulsion droplets. Their large surface area facilitates faster and more complete body absorption. More absorption takes place owing to the finer droplet size and hence larger surface area. However, to form a stable microemulsion when in contact with water, it has been found generally that a blend of high and low HLB surfactants are required.

A series of vehicle compositions of various formulations of SMEDDS were prepared (as described in Tables 2 and 3) with varying concentrations of oil (10-40% by weight), surfactant (20-65% by weight), and cosurfactant (10-70% by weight). Mixtures of oil, surfactant, and cosurfactant were accurately weighed into screw-capped glass vials and heated at 37° C. in a water bath and constantly swirled. In some mixtures, the oil-surfactant-cosurfactant mixture was mixed with Transcutol® P (a solubilizer) at 10:1 weight ratio Visual Observations of Microemulsion Formation To assess the performance of the prepared SMEDDS formulations, a visual test was used to assess the properties of the self-microemulsification. One gram of the self-emulsifying vehicle composition mixture was added to 100 g of water in a glass beaker, all at a constant temperature of 37° C. while stirring. The tendency of the formulations to emulsify spontaneously and the progress of emulsion droplets were also observed. An emulsion was considered to be "good" when the droplets were fine and formed a clear/milky emulsion that is uniformly distributed. An emulsion was considered to be "bad" when there was poor or no emulsion formation with immediate coalescence of oil droplets, especially when this occurred after stirring was stopped.

One method of identifying whether a microemulsion has been formed is to take 1 part of the formulation and dilute in water by 100 times. If the water mix is translucent or clear, it indicates the formation of microemulsion. All excipient systems were diluted with water in the same ratio (×100) and compared according to the appearance from clear to cloudy to phase separation. By comparing the sample sequence with trial formulas, the relationship of excipient ratios to the likelihood of microemulsion formation was established.

Preparation of SMEDDS Formulations

To prepare SMEDDS formulations, components of the SMEDDS formulations (i.e., oil(s), surfactant, cosurfactant and coenzyme Q10 and also a solubilizer if applicable) were accurately weighed into screw-capped glass vials and swirled in a water bath heated to 37° C.

Dissolution Studies

Prepared formulations were weighed into size 0 hardshell capsules for preliminary dissolution studies. Each capsule represents a 30 mg dose of coenzyme Q10. Dissolution profiles of the capsules filled with the self-microemulsifiable formulations were determined using USP Apparatus 2 (paddles) at 37° C. and at a rotating speed of 75 rpm in 1000 mL of water. Capsules were held to the bottom of the vessel using paperclips. Samples were filtered using a 0.45 membrane filter and assayed for the coenzyme Q10 by HPLC. The dissolution experiments were carried out in duplicate.

HPLC Analysis

The coenzyme Q10 was analyzed using a C18, 3.9 mm ID×30 mm column. The mobile phase consisted of 100% methanol and was pumped at a flow rate of 1.5 mL/min.

Examples of Formulations

Once excipient systems were developed, coenzyme Q10 was added at different concentrations to find a physically stable formula that does not recrystallize over time. The formulas were prepared as described above.

Tables 2, 3 and 4 show constituents of respective first, second and third formula series using combinations of oils, surfactants and solvents/solubilizers in various combinations.

TABLE 2

Q10 Trial Formula Series 1

| Description | AT-Q10-5 Parts | AT-L-Q10-5 Parts | A-Q10-5 Parts | A-L-Q10-5 Parts |
| --- | --- | --- | --- | --- |
| Isopropyl myristate | 40 | 20 | 40 | 20 |
| Lemon oil | 0 | 20 | 0 | 20 |
| Span 80 | 10 | 10 | 10 | 10 |
| Polysorbate 80 | 50 | 50 | 50 | 50 |
| Transcutol P | 10 | 10 | 0 | 0 |
| Q10 | 5 | 5 | 5 | 5 |
| Total | 115 | 115 | 105 | 105 |

TABLE 1

Solubility of Coenzyme Q10 (% w/w)

| Sample | Average Absorbance at 405 nm | Exact amount (mg) dissolved in solvent | Sample conc (mg/mL) in solvent | 50 mL sample solution of coenzyme Q10 (mg) | 100 mL sample solution of coenzyme Q10 (mg) | 200 mL sample solution of coenzyme Q10 (mg) | Solubility of coenzyme Q10 (% w/w) |
| --- | --- | --- | --- | --- | --- | --- | --- |
| Lemon oil | 0.88050 | 1054.0 | 1.2791 | — | — | 255.8 | 24.3 |
| Isopropyl myristate | 0.38730 | 1007.7 | 0.56260 | — | — | 112.5 | 11.2 |
| Acetylated monoglycerides | 0.52670 | 1019.8 | 0.76500 | — | 76.50 | — | 7.5 |
| Labrafil M 1944 | 0.82900 | 1018.8 | 1.2040 | 60.21 | — | — | 5.91 |
| Labrafil M 2125 | 0.37300 | 1011.9 | 0.54190 | — | 54.19 | — | 5.35 |
| Oleic acid | 0.26350 | 1006.3 | 0.38300 | — | 38.30 | — | 3.80 |
| Medium chain triglycerides | 0.26000 | 1009.2 | 0.37760 | — | 37.76 | — | 3.74 |
| Span 80 | 0.44480 | 998.10 | 0.64620 | 32.31 | — | — | 3.24 |
| Labrafac Hydro WL1219 | 0.44250 | 1012.6 | 0.64300 | 32.14 | — | — | 3.17 |
| Lauroglyco 190 | 0.42360 | 1005.2 | 0.61500 | 30.77 | — | — | 3.06 |
| Lauroglyco 1 FCC | 0.21720 | 1033.0 | 0.31550 | — | 31.55 | — | 3.05 |
| Glyceryl mono-oleate | 0.33370 | 1003.8 | 0.48500 | 24.24 | — | — | 2.41 |
| PEG 35 Castor oil | 0.30160 | 1005.9 | 0.47280 | 23.64 | — | — | 2.34 |
| Polysorbate 85 | 0.21870 | 1011.4 | 0.31770 | 15.89 | — | — | 1.57 |
| Capmul MCM C8 | 0.20730 | 1001.6 | 0.30110 | 15.05 | — | — | 1.50 |
| Polysorbate 80 | 0.04760 | 1001.6 | 0.07460 | 3.730 | — | — | 0.370 |
| Transcutol P | 0.03560 | 1011.0 | 0.05160 | 2.580 | — | — | 0.260 |

TABLE 3

Q10 Trial Formula Series 2

| Description | AT-Q10-4 Parts | AT-L-Q10-4 Parts | A-Q10-4 Parts | A-L-Q10-4 Parts |
|---|---|---|---|---|
| Isopropyl myristate | 40 | 20 | 40 | 20 |
| Lemon oil | 0 | 20 | 0 | 20 |
| Span 80 | 10 | 10 | 10 | 10 |
| Polysorbate 80 | 50 | 50 | 50 | 50 |
| Transcutol P | 10 | 10 | 0 | 0 |
| Q10 | 4 | 4 | 4 | 4 |
| Total | 114 | 114 | 104 | 104 |

TABLE 4

Q10 Trial Formula Series 3

| Description | AL-13-Q10B Parts | AL-14-Q10B Parts | AL-16-Q10B Parts | AL-17-Q10B Parts |
|---|---|---|---|---|
| Isopropyl myristate | 30 | 25 | 20 | 30 |
| Lemon oil | 10 | 10 | 20 | 10 |
| Span 80 | 5 | 5 | 2.5 | 2.5 |
| Polysorbate 80 | 55 | 60 | 57.5 | 57.5 |
| Q10 | 4.76 | 4.76 | 4.76 | 4.76 |
| Total | 104.76 | 104.76 | 104.76 | 104.76 |

Table 5 shows the fill formulations calculated as 30 mg Q10 per capsules and fill volume.

TABLE 5

Fill Formulas and Fill Volume

| Ingredients | A-L-7-Q10B (mg/cap) | A-L-13-Q10B (mg/cap) | A-L-16-Q10B (mg/cap) | A-L-17-Q10B (mg/cap) | A-L-Q10-5 (mg/cap) |
|---|---|---|---|---|---|
| Isopropyl myristate | 126 | 189 | 126 | 189 | 120 |
| Span 80 | 31 | 32 | 16 | 16 | 60 |
| Polysorbate 80 | 346 | 347 | 362 | 362 | 300 |
| Lemon Oil | 126 | 63 | 126 | 63 | 120 |
| Coenzyme Q10 | 30 | 30 | 30 | 30 | 30 |
| Fill weight (mg) | 660 | 662 | 660 | 659 | 630 |
| Fill volume (minim) | 11.2 | 11.2 | 11.2 | 11.1 | 10.7 |

Dosage formulations prepared in accordance with the present invention compare favorably with the best coenzyme Q10 formulations presently known in market: Ogel and Maxisorb. The fill weights of the currently offered formulations in the market containing 30 mg of Q10 are approximately 900 mg per capsule. The formulations, prepared in accordance with the present invention yield fill weights that are substantially less, about 660 mg, to deliver the same amount of active ingredient. Therefore, the present invention offers the possibility of using capsule sizes that are smaller than the best commercial comparative products. This makes the capsule easier to swallow. Viewed from the perspective of capsule size, higher levels of active ingredient may be offered in a capsule size that is the same as lower levels of commercially prepared products.

Instrumental Analysis of Droplet Size

The droplet sizes of selected formulations in water were measured with a Zetasizer 3000. Some of the results from the prepared formulations are presented in

TABLE 6

Droplet Sizes of Microemulsions

| Samples | Diameter Volume mean (nm) |
|---|---|
| A-Q10-4 | 36.3 |
| AL-16-Q10-B | 30.7 |
| AL-17-Q10-B | 34.1 |

The results confirmed that the formulations in Table 6 produced microemulsions.

Dissolution Study in Hard Shell Capsules

The fill samples containing 30 mg of Q10 were weighed into hard shells for dissolution study, to simulate dissolution from a soft capsule. Hard shell samples were anchored at the bottom of dissolution flasks by paper clips. All samples contain 30 mg of coenzyme Q10 per capsule. The best two commercial samples, Q-Gel and Maxisorb products, were tested in parallel. A summary of dissolution results is provided in Table 7 below. The dissolution conditions were USP apparatus 2 (paddles); stirring at 75 RPM in 1000 mL of water. Samples were taken at 15, 30, 45 and 60 minutes and filtered through 0.45 micro filter.

TABLE 7

Dissolution results

| Samples | Fill weight (mg) | Capsule size (die) minims | Max % release | Time at max % release (min) |
|---|---|---|---|---|
| A-Q10-4 | 780 | 16 | 100 | 15 |
| A-Q10-5 | 630 | 12 | 97 | 30 |
| AT-Q10-4 | 857 | 16 | 91 | 45 |
| AT-L-Q10 | 502 | 11 | 84 | 45 |
| Q-gel | 896 | 16 | 94 | 60 |
| Maxisorb | ~900 | 16 | 99 | 30 |

Sample A-Q10-4 released 100% of Q10 within 15 minutes. Considering that conventional soft capsule formulations of coenzyme Q10 in oils and suspensions have zero dissolution, the results obtained by the inventive formula are excellent and surprising. Taking into account that hard shells rupture slightly faster than soft capsule capsules due to differences in capsule wall thickness, the dissolution of A-Q10-4 is better than or at least comparable to benchmark products Qgel and Maxisorb in terms of release speed and percent of the active. It should be noted that the release of the active ingredient (i.e., coenzyme Q10) appears to be directly related to the clarity of the emulsions. The clearer the emulsion, the faster and more completely it releases Q10.

The clarity of the emulsion is related to the size of droplets. Naked eyes can distinguish droplets as low as about 15 micron, seen as cloudy liquid. When the droplets are down to nanometer range, particularly below 100 nm which are in the range of microemulsions, translucent or clear liquids are seen. In fact, formulation A-Q10-4 in water produced the clearest liquid among trial samples in Table 7. This formulation was shown to be a microemulsion by instrumental analysis. Therefore, one can conclude that the dramatic improvement of coenzyme Q10 dissolution is due to the formation of a microemulsion.

Storage Stability of Formulations

Recrystallization of Q10 from liquid phase could take days or weeks due to its low melting point. To eliminate recrystallization for better shelf life, while still maintaining optimum dissolution properties, additional experiments were conducted to identify physically stable dosage formulations. The samples were found free of recrystallined COENZYME Q10 as set forth in Table 8.

TABLE 8

Storage Stability of Formulations

| Samples | Number of days free of crystals |
|---|---|
| A-L-Q10-5 | More than 80 days |
| A-L-Q10-4 | More than 80 days |
| AT-L-Q10-4 | More than 80 days |
| AL-16-Q10-B | More than 30 days |

Encapsulation in Soft Capsules

The optimized fill formulation has been successfully encapsulated in soft gelatin capsules and soft vegetarian capsules (Vegicaps®, Cardinal Health 409, Inc.) The composition of Vegicaps and process of making soft capsules therewith is disclosed in U.S. Pat. No. 6,337,045.

Industrial Applicability

In summary, new Self-Micro-Emulsifying Drug Delivery Systems have been developed for coenzyme Q10 soft capsules. Typical formulations are composed of Lemon oil, Isopropyl myristate, Polysorbate 80 and Span 80 as excipients. It may also contain Transcutol P as a solubilizer. However, excipients are not limited to those mentioned ingredients. The method of formulation is also suitable for other poorly water soluble substances. Other excipient mixtures can be constructed by using the principles explained herein and is within the ability of one skilled in the art. The formulations displayed excellent dissolution properties, fast and maximum release of the coenzyme Q10 active ingredient. The fill formula is storage stable, and provides the added advantage that the capsule size would be smaller than the best presently available commercial samples containing the same amount of active ingredient.

The foregoing demonstrates that the present invention offers advantages over prior formulations including eliminating some of the disadvantages of those formulations. The soft capsule formulations of the present invention offer a new Self-Microemulsifying Drug Delivery System (SMEDDS) for coenzyme Q10 that is better than commercial oil solution or suspension formulations. The formulations of the present invention displayed substantial solubilization in water and maximum dissolution up to 100%. Conventional soft capsule products have zero or very low dissolution.

Apart from excellent dissolution properties, formulations of the present invention have the additional advantage of achieving smaller capsule size for the same dosage level, and the fill weights are at least 100 mg less than Q-Gel and Maxisorb (refer to Table 6). When capsule sizes are the same, the present inventive formulations allow higher levels of the active to be supplied. Smaller capsules are easier to swallow particularly for children and older people.

Furthermore, the manufacture of the fill formulations of the present invention is relatively simple and only requires standard mixing and heating equipment, while conventional emulsion methods require high energy input and shearing during processing. The fill formulations of the present invention are also physically stable without recrystallization during storage. Stable shelf life is critical for commercialization.

Solubility and dissolution are the limiting factors in bioavailability of coenzyme Q10. These factors have been successfully overcome by the SMEDDS developed in accordance with the present invention. Therefore, the bioavailability of the formulations of the present invention is expected to have higher bioavailability than prior art formulations. The principle, methodology and formulations developed in this application are not limited to coenzyme Q10. They are also applicable to other poorly water soluble pharmaceutical active ingredients for improving dissolution and bioavailability.

Having thus described the present invention in detail, it will be obvious to those skilled in the art that various changes or modifications may be made without departing from the scope of the invention defined in the appended claims and described in the specification.

What is claimed is:

1. A soft capsule containing an active ingredient comprising the active ingredient contained in a stable self-microemulsifying mixture, said mixture comprising:
    (1) at least one hydrophilic surfactant having a hydrophile-lipophile balance of greater than 12;
    (2) at least one lipophilic co-surfactant having a hydrophile-lipophile balance of less than 8; and
    (3) at least one hydrophobic solvent;
    wherein the weight ratio of said at least one hydrophilic surfactant to said at least one lipophilic co-surfactant is in the range of from 30:1 to 3:1;
    wherein the concentration of said at least one hydrophobic solvent in said self-microemulsifying mixture is in the range of from 2 to 50% by weight and comprises a mixture of isopropyl myristate and lemon oil or a mixture of isopropyl myristate and orange oil; and
    wherein the self-microemulsifying mixture exhibits a dissolution of up to 100% and storage stability of more than 80 days.

2. The soft capsule according to claim 1, wherein the concentration of said at least one hydrophilic surfactant in said self-microemulsifying mixture is in the range of from 20 to 70% by weight.

3. The soft capsule according to claim 1, wherein the concentration of said at least one lipophilic co-surfactant in said self-microemulsifying mixture is in the range of from 1.5 to 50% by weight.

4. The soft capsule according to claim 1, wherein said mixture is substantially free of water.

5. The soft capsule according to claim 1 additionally comprising optionally at least one hydrophilic solvent.

6. The soft capsule according to claim 5, wherein said at least one hydrophilic solvent is selected from the group consisting of glycol ethers.

7. The soft capsule according to claim 5, wherein the weight ratio of said hydrophilic solvent to the total of said at least one hydrophilic surfactant, said at least one lipophilic co-surfactant and said at least one hydrophobic solvent is about 0.02-1:1.

8. A soft capsule containing a dosage form of a low water-solubility active ingredient comprising: at least one low water-solubility active ingredient contained in a stable self-microemulsifying mixture, said mixture comprising:
    (1) at least one hydrophilic surfactant having a hydrophile-lipophile balance of greater than 12;

(2) at least one lipophilic co-surfactant having a hydrophile-lipophile balance of less than 8; and (3) at least one hydrophobic solvent wherein the weight ratio of said at least one hydrophilic surfactant to said at least one lipophilic co-surfactant is in the range of from 30:1 to 3:1;

wherein the concentration of said at least one hydrophobic solvent in said self-microemulsifying mixture is in the range of from 2 to 50% by weight and comprises a mixture of isopropyl myristate and lemon oil or a mixture of isopropyl myristate and orange oil; and wherein the self-microemulsifying mixture exhibits a dissolution of up to 100% and storage stability of more than 80 days.

9. A soft capsule containing a dosage form of coenzyme Q10 comprising: coenzyme Q10 contained in a stable self-microemulsifying mixture, said mixture comprising:

(1) at least one hydrophilic surfactant having a hydrophile-lipophile balance of greater than 12;

(2) at least one lipophilic co-surfactant having a hydrophile-lipophile balance of less than 8; and (3) at least one hydrophobic solvent;

wherein the weight ratio of said at least one hydrophilic surfactant to said at least one lipophilic co-surfactant is in the range of from 30:1 to 3:1;

wherein the concentration of said at least one hydrophobic solvent in said self-microemulsifying mixture is in the range of from 2 to 50% by weight and comprises a mixture of isopropyl myristate and lemon oil or a mixture of isopropyl myristate and orange oil; and wherein the self-microemulsifying mixture exhibits a dissolution of up to 100% and storage stability of more than 80 days.

10. The soft capsule according to claim 9, wherein the capsule wall is a non-gelatin composition.

* * * * *